United States Patent
Kanbayashi et al.

(10) Patent No.: US 10,234,387 B2
(45) Date of Patent: Mar. 19, 2019

(54) OPTICAL ANALYSIS SYSTEM AND OPTICAL ANALYSIS METHOD

(71) Applicant: Hitachi, Ltd., Chiyoda-ku, Tokyo (JP)

(72) Inventors: Takuya Kanbayashi, Tokyo (JP); Shinichi Taniguchi, Tokyo (JP); Akihiro Nojima, Tokyo (JP); Yusuke Kaga, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/833,075

(22) Filed: Dec. 6, 2017

(65) Prior Publication Data

US 2018/0172584 A1 Jun. 21, 2018

(30) Foreign Application Priority Data

Dec. 15, 2016 (JP) ................................. 2016-242988

(51) Int. Cl.
 *G01N 21/53* (2006.01)
 *G01N 21/01* (2006.01)
 *G01N 21/17* (2006.01)

(52) U.S. Cl.
 CPC .......... *G01N 21/534* (2013.01); *G01N 21/01* (2013.01); *G01N 21/1717* (2013.01); *G01N 2021/1729* (2013.01); *G01N 2201/023* (2013.01)

(58) Field of Classification Search
 CPC .......... G01N 21/59; G01N 2021/5969; G01N 21/51; G01N 2021/513; G01N 2021/516; G01N 21/534
 See application file for complete search history.

(56) References Cited

U.S. PATENT DOCUMENTS

| | | | | |
|---|---|---|---|---|
| 3,695,763 A * | 10/1972 | Shiuh | ...................... | G01N 15/08 250/575 |
| 3,806,259 A * | 4/1974 | Boostrom | ................. | G01J 3/02 356/244 |
| 4,166,703 A * | 9/1979 | Kirsch | ................... | G01N 15/08 250/573 |
| 4,291,983 A * | 9/1981 | Kraft | ...................... | C12M 41/36 250/574 |
| 4,762,413 A * | 8/1988 | Namba | ................ | G01N 21/253 250/574 |
| 2012/0086938 A1* | 4/2012 | Folkenberg | .......... | G01N 1/4077 356/246 |
| 2013/0222805 A1* | 8/2013 | Wustefeld | .............. | G01N 21/15 356/432 |

FOREIGN PATENT DOCUMENTS

JP     2014-115268 A    6/2014

* cited by examiner

*Primary Examiner* — Tri Ton
*Assistant Examiner* — Rufus Phillips
(74) *Attorney, Agent, or Firm* — Crowell & Moring LLP (57) ABSTRACT

The invention optically analyzes a component in a sample having a material suspended. An optical analysis system that irradiates a liquid sample with light and analyzes a component of the sample using transmitted light transmitted through the sample includes a container accommodating the sample and an ultrasonic irradiation unit irradiating an ultrasonic wave for exciting the sample. The container includes a pair of light transmission wall portions between which the sample is disposed and which has light transmissivity, and one of the light transmission wall portions and the other of the light transmission wall portions are disposed to be separated from each other at a distance shorter than a wavelength of the ultrasonic wave.

8 Claims, 10 Drawing Sheets

OPTICAL ANALYSIS SYSTEM AND OPTICAL ANALYSIS METHOD

TECHNICAL FIELD

The present invention relates to an optical analysis system and an optical analysis method.

BACKGROUND ART

In the related art, an optical analysis apparatus that irradiates a sample with light and analyzes a component contained in the sample using transmitted light transmitted through the sample is known. For example, in PTL 1, "A spectrometric analysis apparatus which has a function of measuring absorbance of a target sample and in which an optical system for measuring the absorbance of the sample includes a light transmitting unit in which a container storing the sample is disposed, an illumination unit including a light source for irradiating the sample stored in the container of the light transmitting unit, a photometric unit that spectrally separates transmitted light from the sample stored in the container of the light transmitting unit and detects intensity for each wavelength thereof so as to measure the absorbance of the sample, and a first optical fiber connecting the illumination unit and the light transmitting unit and guiding the illumination light, and in which partial polarization property of the illumination light of the light source is eliminated by the first optical fiber so as to cause the sample to be irradiated with the illumination light as non-polarized light" is described.

CITATION LIST

Patent Literature

PTL 1: JP-A-2014-115268

SUMMARY OF INVENTION

Technical Problem

However, in a case where a suspended sample having a suspended material contained is analyzed, it is unable to accurately detect transmitted light and accurately analyze the component of the sample in the technology disclosed in PTL 1. Specifically, in the spectrometric analysis apparatus disclosed in PTL 1, an amount of the component contained in the sample is quantified based on a distance (optical path length) through which light is transmitted through the sample and absorbance of the component which becomes an analysis target. In a case where a suspended material (scatterer) scattering light exists within the sample, incident light is not transmitted through the sample, or, incident light is subjected to multiple scattering by a scatterer and an optical path length is changed. For that reason, it is unable to accurately analyze the component contained in the sample having a material suspended.

An object of the present invention is to optically analyze the component in the sample having a material suspended.

Solution to Problem

Although the present application includes a plurality of means for solving at least some of the problems described above, examples thereof are as follows.

According to one aspect of the present invention for solving the problems described above, there is provided an optical analysis system that irradiates a liquid sample with light and analyzes a component of the sample using transmitted light transmitted through the sample, and the optical analysis system includes a container accommodating the sample and an ultrasonic irradiation unit irradiating an ultrasonic wave for exciting the sample, and the container includes a pair of light transmission wall portions between which the sample is disposed and which has light transmissivity and one of the light transmission wall portions and the other of the light transmission wall portions are disposed to be separated from each other at a distance shorter than a wavelength of the ultrasonic wave.

Advantageous Effects of Invention

According to one aspect of the present invention, it is possible to optically analyze the component in the sample having a material suspended.

Problems to be solved, configurations, and effects other than those described above are clarified by the following description of embodiments.

DESCRIPTION OF EMBODIMENTS

In the following, a plurality of embodiments of the present invention will be described with reference to the drawings. In description of configurations of respective embodiments, three axes (X, Y, and Z) perpendicular to each other are used for the understanding of the invention. The configurations of respective embodiments are allowed to be changed within a range in which substantially the same effects are achieved even without being strictly coincident with X, Y, and Z axes.

[First Embodiment]

Figure 1:
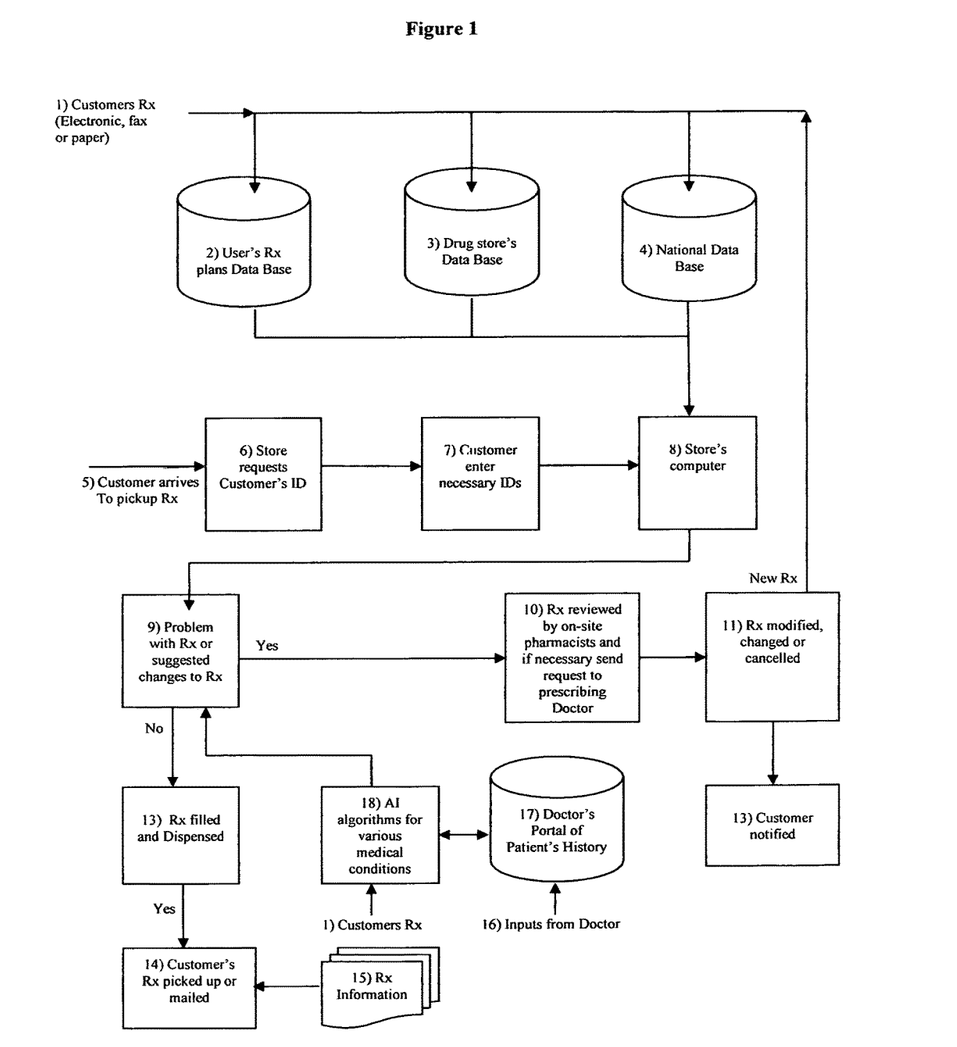
FIGS. 1A and 1B are diagrams illustrating an example of a configuration of an optical analysis system according to a first embodiment of the present invention.

FIG. 1 is a diagram illustrating an example of a configuration of an optical analysis system according to a first embodiment. An optical analysis system 100 includes a light source 10, a container 21, an ultrasonic irradiation unit 22, a control unit 23, and a light receiving unit 30.

The container 21 accommodates a liquid sample 1 which is a target of component analysis by the optical analysis system 100. The sample 1 is a suspension obtained by dispersing a solid suspended material in a liquid. The container 21 is formed in a rectangular parallelepiped shape. The container 21 is formed by using, for example, a transparent material such as glass.

In detail, the container 21 includes a pair of light transmission wall portions (parallel to the XZ plane) between which a sample 1 is disposed and which has light transmissivity. The container 21 includes a pair of wall portions (first wall portion and second wall portion parallel to the YZ plane) disposed perpendicularly to the pair of the light transmission wall portions between which the sample 1 is disposed. The light source 10 and the light receiving unit 30 are disposed at, for example, both outer sides of the pair of the light transmission wall portions so that light emitted from the light source 10 passes through a light transmission wall portion located at a near side, the sample 1, and a light transmission wall portion located at a far side in this order in the Y direction to reach the light receiving unit 30.

The container 21 is configured so that the sample 1 is exchangeable. For example, the container 21 may include an opening for taking in and out the sample 1 and a lid member capable of closing and opening the opening.

The ultrasonic irradiation unit 22 has a flat oscillation surface and the oscillation surface is arranged to abut on an exterior wall surface (surface located at a side opposite to sample 1) of the first wall portion. The ultrasonic irradiation unit 22 is connected to the control unit 23 and is driven by an electrical signal E output from the control unit 23. The driven ultrasonic irradiation unit 22 oscillates an oscillation surface (parallel to the YZ plane) thereof to irradiate an ultrasonic wave in the X direction and excites the sample 1 accommodated in the container 21. Light and the ultrasonic wave are set indifferent directions (directions perpendicular to each other) to be directed. The ultrasonic irradiation unit 22 is configured to include, for example, a piezoelectric ultrasonic oscillator.

The light source 10 emits light for allowing the sample 1 to be irradiated therewith. Light emitted from the light source 10 is transmitted through the pair of the light transmission wall portions and the sample 1 between the light transmission wall portions and is received in the light receiving unit 30. The light source 10 is connected to the control unit 23 and is controlled by the control unit 23. The light source 10 can be realized by using, for example, a light emitting element such as a light emitting diode (LED).

The light receiving unit 30 receives light transmitted through the pair of the light transmission wall portions and the sample 1 between the light transmission wall portions. The light receiving unit 30 outputs, for example, an electrical signal indicating intensity of received light to the control unit 23. The light receiving unit 30 can be realized by using, for example, a light receiving element such as a photodiode.

The control unit 23 executes a process for analyzing the component contained in the sample 1 based on, for example, intensity of transmitted light output from the light receiving unit 30, in addition to controlling the light source 10, the ultrasonic irradiation unit 22, and the light receiving unit 30. The control unit 23 can be realized by, for example, a microcomputer, such as for example, a central processing unit (CPU), a random access memory (RAM) or a dedicated hardware circuit.

The optical analysis system 100 of the present embodiment irradiates the sample 1 with the ultrasonic wave so as to make it possible to flocculate the suspended material within the sample 1. The optical analysis system 100 can form a transparent region other than a flocculation region (also, referred to as a suspension region), in which the suspended material is flocculated, within the sample 1 and cause light to be transmitted through the transparent region. In the optical analysis system 100 of the present embodiment, a distance L between inner wall surfaces of the pair of the light transmission wall portions is set to be shorter than a wavelength of the ultrasonic wave output from the ultrasonic irradiation unit 22. These configurations will be described later in detail using FIG. 2 to FIG. 4.

The ultrasonic irradiation unit 22 may be provided on an exterior wall surface of the second wall portion. Two ultrasonic irradiation units 22 may be respectively provided on the exterior wall surfaces of the first wall portion and the second wall portion. Two ultrasonic irradiation units 22 are provided to increase sound pressure of the ultrasonic wave so as to make it easy to flocculate the suspended material within the sample 1.

Figure 2A:
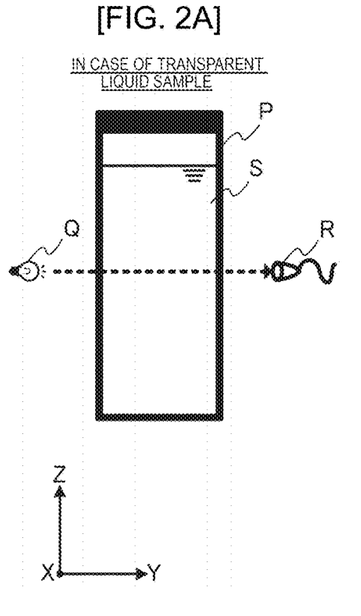
FIGS. 2A and 2B are explanatory diagrams for explaining an advancing state of light irradiated from a light source.
Figure 2B:
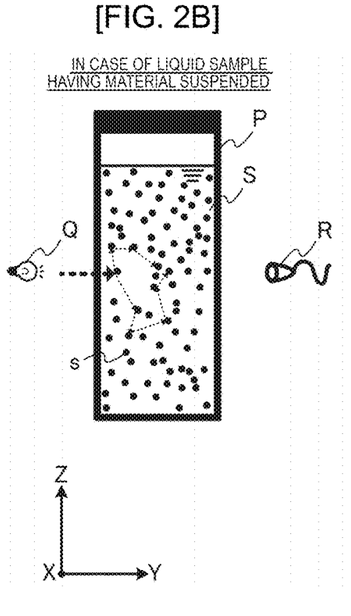

Description will be made on problems in analyzing the liquid sample having a material suspended with reference to FIG. 2. FIG. 2 is an explanatory diagram for explaining an advancing state of light irradiated from the light source. In FIG. 2, a liquid sample S is accommodated in a container P and a light source Q and a light receiving unit R are disposed at both sides of a pair of light transmission wall portions of the container P. FIG. 2(a) illustrates a case where the sample S is transparent. FIG. 2(b) illustrates a case where the sample S is a suspension in which the suspended material s (also, referred to as a scatterer) scattering light is contained.

As illustrated in FIG. 2(a), light beams irradiated from the light source Q reach the light receiving unit R after a portion of the light beams are absorbed by the component contained in the sample S at the time when the light beams are transmitted through the sample S. The wavelength and amount of the absorbed light beams become different according to the component and thus, characteristics of light beams reached the light receiving unit R are analyzed so as to make it possible to specify the component contained in the sample S. The amount of the absorbed light beams depends on the amount of the component contained in the sample S and thus, a distance (also, referred to as an optical path length) through which light advances within container P is fixed so as to make it possible to perform quantitative analysis of the component. Accordingly, in a case where the sample S is transparent, light advances straightly such the optical path length becomes constant and quantitative analysis of the component can be accurately performed.

On the other hand, as illustrated in FIG. 2(b), in a case where the sample S is a suspension, light irradiated from the light source Q is prevented from advancing by a suspended material s and does not reach the light receiving unit R, or is subjected to multiple scattering by suspended material s. That is, the optical path length that light advances within the container P does not become constant. For that reason, it is unable to perform quantitative analysis of the component contained in the sample S or to accurately perform quantitative analysis of the component contained in the sample S.

The optical analysis system 100 according to the present embodiment is configured to avoid prevention of advancing of light by scatterers. That is, the optical analysis system 100 irradiates the sample 1 having a material suspended with the ultrasonic wave so as to generate the transparent region, in which the scatterers are less, within the sample 1 and irradiate the transparent region with light.

Figure 3:
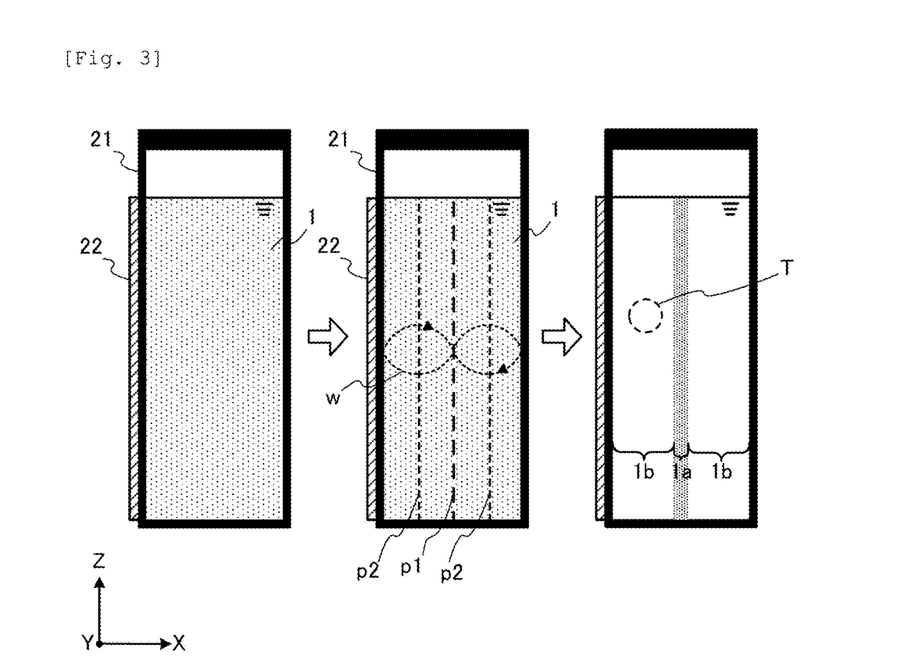
FIG. 3 is a diagram illustrating an operation principle of the optical analysis system according to the first embodiment of the present invention.

FIG. 3 is a diagram illustrating an operation principle of the optical analysis system according to the first embodiment. FIG. 3 schematically illustrates a phenomenon inside the container 21 when seen from the Y direction. The left diagram of FIG. 3 illustrates a state before irradiation of the ultrasonic wave and the central diagram and the right diagram illustrate a state after irradiation of the ultrasonic wave.

The ultrasonic wave irradiated from the driven ultrasonic irradiation unit 22 in the X direction generates a standing wave w in the sample 1 having a material suspended. A sound field according to the natural frequency of the irradiated ultrasonic wave is formed in the sample 1 by the standing wave w. The standing wave w is the oscillation in which a node p1 which corresponds to an area having high sound pressure and an antinode p2 which corresponds to an area having low sound pressure periodically appear. The node p1 and the antinode p2 are formed in a surface shape in the YZ direction and are arranged in the X direction at intervals.

When the standing wave w is developed, suspended materials (multiple points in the drawing) which are sufficiently smaller than a gap between the node p1 and the antinode p2 receive a force (acoustic radiation force) directed to the node p1 or the antinode p2 according to a physical property value such as mass of the materials and are flocculated at the position of the node p1 or antinode p2. In the right diagram, the suspended materials are flocculated at the node p1 and in the periphery thereof (also, similar in the following description). As such, a flocculation region 1a in which a lot of flocculated suspended materials are contained and a transparent region 1b in which less suspended materials are contained periodically appear within the container 21. The suspended materials may not be contained in the transparent region 1b.

The optical analysis system 100 of the present embodiment is configured such that light irradiated from the light source 10 passes through a measurement region T within the transparent region 1b formed as described above in the Y direction and light passed through the measurement region T is received by the light receiving unit 30. Transmitted light is transmitted through the transparent region 1b such that transmitted light may reach the light receiving unit 30 without being almost scattered. With this, even in the sample having a material suspended, it becomes possible to accurately and quantitatively analyze the component contained in the sample.

Figure 4A:
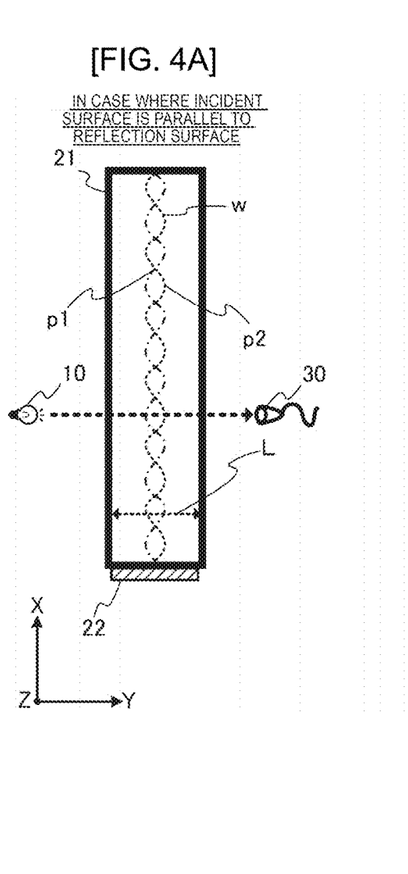
FIGS. 4A and 4B are explanatory diagrams for explaining a relationship between an ultrasonic wave and a transparent region.
Figure 4B:
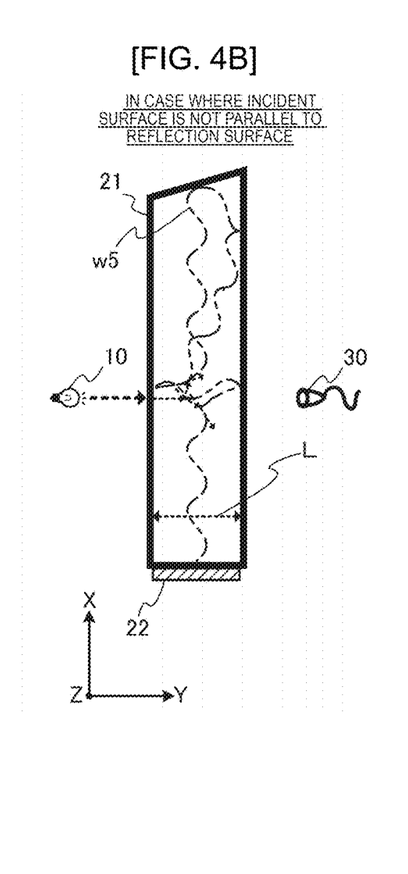

With reference to FIG. 4, descriptions will be made on a case where a distance L between inner wall surfaces of the pair of the light transmission wall portions is set to be longer than the wavelength of the ultrasonic wave. FIG. 4 is an explanatory diagram for schematically explaining a relationship between the ultrasonic wave and the transparent region. The distance L between the inner wall surfaces of the pair of the light transmission wall portions of the container 21 is set to be longer than the wavelength of the ultrasonic wave.

FIG. 4(a) illustrates a case where an incident surface (inner wall surface of the first wall portion on which the ultrasonic irradiation unit 22 is provided) of the container 21 is parallel to a reflection surface (inner wall surface of the second wall portion opposing first wall portion) of the container 21. An oscillation surface (emission surface) of the ultrasonic irradiation unit 22 is parallel to the incident surface and the reflection surface. In this case, when an incident wave advancing (X direction) vertically to the reflection surface is reflected on the reflection surface, the reflected wave of which the direction (X direction) opposite to the incident wave is generated and the reflected wave and the incident wave are combined such that the standing wave w is generated. The node p1 and the antinode p2 are periodically formed in the X direction by the standing wave w and thus, the flocculation region and the transparent region (not illustrated) are also periodically formed. A sufficiently wide transparent region which allows light to transmit straightly through from the light source 10 to the light receiving unit 30 is formed.

FIG. 4(b) illustrates a case where the incident surface of the container 21 is not parallel to the reflection surface thereof. The oscillation surface of the ultrasonic irradiation unit 22 is parallel to the incident surface. In this case, when the incident wave is reflected on the reflection surface, a reflected wave which comes off obliquely to the advancing direction (X direction) of the incident wave is generated. Furthermore, the reflected wave is reflected on the inner wall surfaces the light transmission wall portions. Then, a random wave w5 which does not have periodicity is generated, the node and the antinode are formed at random positions within the container 21, and furthermore, the flocculation region and the transparent region are formed at various positions within the container 21 in various shapes and directions. As a result, a sufficiently wide transparent region which allows light to transmit straightly through is not formed. More specifically, nodes of the wave w5 are generated in various directions (for example, Y direction) intersecting with the X direction and the flocculation region is also generated in these directions. Light from the light source 10 is prevented by the randomly formed flocculation region and component analysis cannot be performed.

Here, in the optical analysis system 100 of the present embodiment, as described above, the distance L (optical path length L) between the inner wall surfaces of the pair of the light transmission wall portions is set to be shorter than the wavelength of the ultrasonic wave or the wavelength of the ultrasonic wave is set to be longer than the distance L. In this case, the reflected wave obliquely reflected on the reflection surface is reflected on another inner wall surface before a node is formed, and further, the reflection is repeated. That is, nodes of the random wave are not generated in various directions (for example, the Y direction) intersecting with the X direction, or fewer nodes are generated. Following this, flocculation regions are also not generated in various directions (for example, the Y direction) intersecting with the X direction, or fewer flocculation regions are generated. With this, even when the incident surface of the container 21 is not parallel to the reflection surface thereof, a sufficiently wide transparent region which allows light to transmit straightly through from the light source 10 to the light receiving unit 30 is formed.

Figures 5A, 5B:
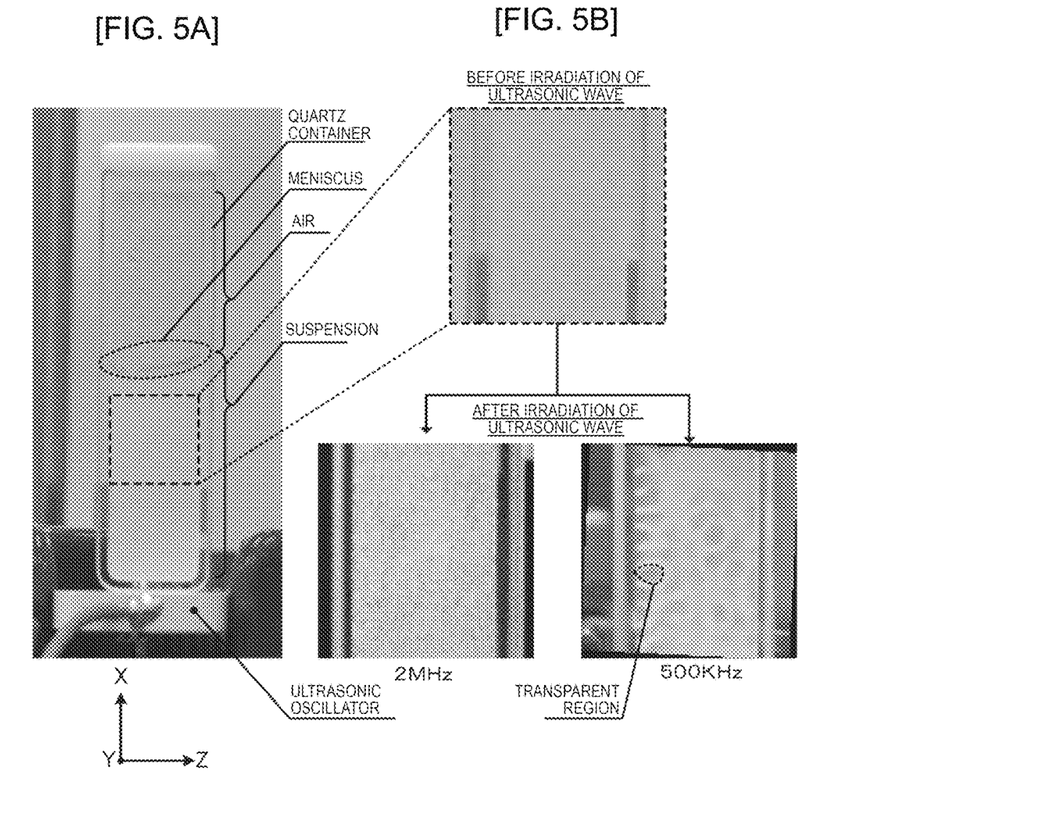
FIGS. 5A and 5B are diagrams for explaining an example of the first embodiment of the present invention.

FIG. 5 is a diagram for explaining an example of the first embodiment of the present invention. The present example is a referential example evaluating formation of the transparent region.

As illustrated in FIG. 5(a), a quartz container is prepared as the container 21 and two kinds of ultrasonic oscillators are used as the ultrasonic irradiation unit 22 in the present example.

The quartz container is formed of a transparent glass material and formed with the outer shape dimension of 45 mm (X)×3.5 mm (Y)×12.5 mm (Z) and the inner shape dimension of 40 mm (X)×1 mm (Y)×10 mm (Z). The distance L (optical path length L) between the pair of the light transmission wall portions parallel to the XZ plane of the quartz container is set to 1 mm. In evaluation performed in the present example, a dispersion ($4.55 \times 10^7$ particles/ml) in which polystyrene particles (particle diameter: 20 μm) are dispersed in water is accommodated in the quartz container as a sample of a suspension.

Each ultrasonic oscillator is used by allowing the oscillation surface thereof to be abutted on an exterior wall surface (parallel to the YZ plane) of a bottom portion of the quartz container. Each ultrasonic oscillator is a piezoelectric ceramic (PZT) ultrasonic oscillator. In the example, two kinds of ultrasonic oscillators (resonance frequencies: 2 MHz and 500 kHz) of which the resonance frequencies are different are used. Each ultrasonic oscillator is driven by an electrical signal of 35 $V_{pp}$.

As illustrated in FIG. 5(a), in evaluation performed in the present example, a suspension and air are stored in the quartz container. For that reason, an interface between air and the suspension is the reflection surface of the ultrasonic wave (X direction). A meniscus is formed on the interface between air and the suspension by interaction between the inner wall surfaces of the quartz container and the suspension. For that reason, the inner wall surface (parallel to the YZ plane) of the bottom portion of the quartz container and the oscillation surface (parallel to the YZ plane) of the ultrasonic oscillator are not parallel to the reflection surface of the ultrasonic wave.

In the upper diagram of FIG. 5(b), a situation of the suspension within the quartz container before irradiation of the ultrasonic wave is illustrated. In this state, the suspension has white turbidity due to uniformly dispersed polystyrene particles.

In the lower left diagram of FIG. 5(b), a situation of the suspension within the quartz container after the ultrasonic wave is irradiated using the ultrasonic oscillator (resonance frequency: 2 MHz) is illustrated. In the lower right diagram of FIG. 5(b), a situation of the suspension within the quartz container after the ultrasonic wave is irradiated using the ultrasonic oscillator (resonance frequency: 500 kHz) is illustrated. In any case, polystyrene particles are flocculated by the acoustic radiation force of the ultrasonic wave in the suspension and the suspension is separated into the transparent region and the flocculation region. The transparent region and the flocculation region of the suspension appear as having a difference in density. A deep gray region corresponds to the transparent region.

The wavelength of the ultrasonic wave having a resonance frequency of 2 MHz is approximately 0.75 mm which is shorter than the optical path length L (1 mm). As described above, the reflection surface of the ultrasonic wave is not parallel to the oscillation surface of the ultrasonic oscillator and thus, in a case where the ultrasonic wave of 2 MHz is irradiated in the X direction, the nodes are also generated in various directions (for example, the Y direction) intersecting with the X direction of the quartz container and the flocculation regions are also generated in these directions according to generation of the node. As illustrated in the lower left diagram of FIG. 5(b), the flocculation regions generated in the directions appears as having fine density.

In contrast, the wavelength of the ultrasonic wave having a resonance frequency of 500 kHz is approximately 3 mm which is longer than the optical path length L (1 mm). For that reason, in a case where the ultrasonic wave of 500 kHz is irradiated in the X direction, the nodes are not generated in various directions (for example, the Y direction) intersecting with the X direction of the quartz container or fewer nodes are generated in the directions. As illustrated in the lower right diagram of FIG. 5 (b), a periodic transparent region having regularity compared to that of the lower left diagram appears as having density.

From the example described above, even in a case where the emission surface of the ultrasonic wave is not parallel to the reflection surface thereof, it is found out that the optical path length L is set to be shorter than the wavelength of the ultrasonic wave or the wavelength of the ultrasonic wave is set to be longer than the optical path length L so as to make it possible to more accurately form the transparent region which allows light to pass through.

Until now, the first embodiment of the present invention was described. According to the present embodiment, it is possible to accurately analyze the component in the sample having a material suspended.

[Second Embodiment]

An optical analysis system according to a second embodiment holds a container using a container holding unit. In the following, description will be mainly made on differences between the second embodiment and the first embodiment.

Figure 6A:
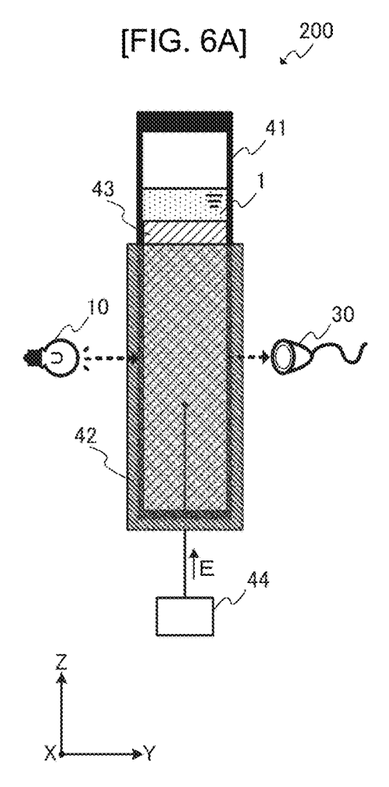
FIGS. 6A and 6B are diagrams illustrating an example of a configuration of an optical analysis system according to a second embodiment of the present invention.
Figure 6B:
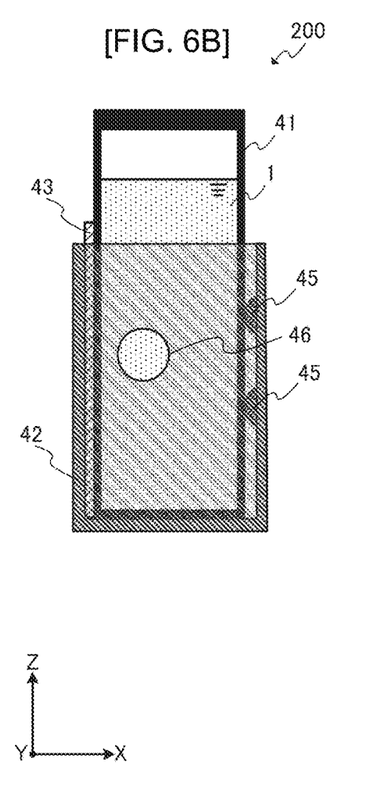

FIG. 6 is a diagram illustrating an example of a configuration of an optical analysis system according to the second embodiment. In FIG. 6, a container holding unit 42 which will be described later is illustrated in such a way that the inside thereof can be seen through. An optical analysis system 200 includes the light source 10, a container 41, a container holding unit 42, an ultrasonic irradiation unit 43, a control unit 44, and the light receiving unit 30. The configurations of the light source 10, the container 41, the ultrasonic irradiation unit 43, the control unit 44, and the light receiving unit 30 are the same as those of the first embodiment.

The container holding unit 42 is formed in a rectangular parallelepiped shape having an opening (at an upper side of the diagram) for detachably holding the container 41 inside thereof. In detail, the container holding unit 42 includes a pair of light transmission wall portions (parallel to the XZ plane) between which the held container 41 is disposed. The container holding unit 42 includes a pair of wall portions (first holding wall portion and second holding wall portion parallel to the YZ plane) disposed perpendicularly to the pair of the light transmission wall portions between which the held container 41 is disposed.

A pair of openings 46 is formed on the pair of the light transmission wall portions. The pair of the openings 46 is disposed in the Y direction so as to oppose each other. The light source 10 and the light receiving unit 30 are disposed at, for example, both outer sides of the pair of the light transmission wall portions so that light emitted from the light source 10 passes through the opening 46 located at a near side, a light transmission wall portion located at a near side of the container 41, the sample 1, a light transmission wall portion located at a far side of the container 41, and the opening 46 located at a far side in this order in the Y direction to reach the light receiving unit 30.

The container holding unit 42 can be formed of, for example, materials such as opaque glass or resin. Thus, light other than transmitted light, which is emitted from the light source 10 and is received by the light receiving unit 30, is excluded or reduced and thus, it is possible to improve accuracy of component analysis.

Figure 7A:
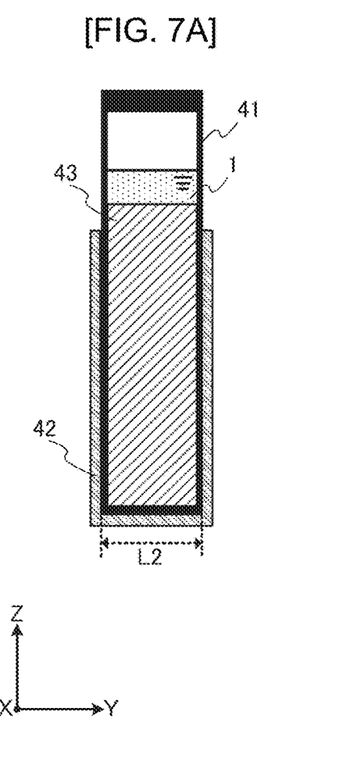
FIGS. 7A and 7B are diagrams illustrating an example of an internal configuration of a container holding unit according to the second embodiment of the present invention.
Figure 7B:
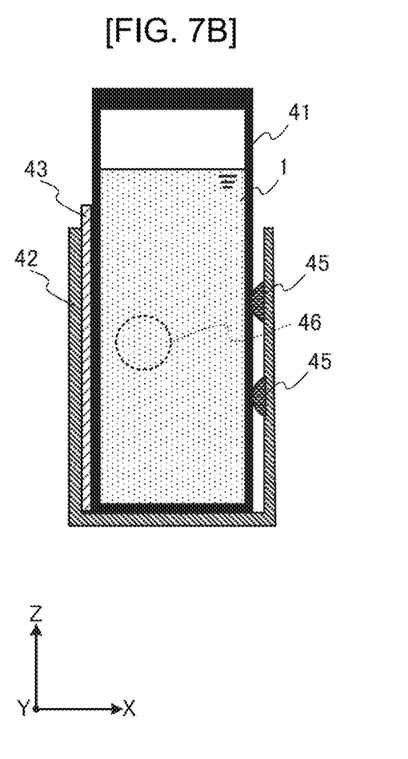

FIG. 7 is a diagram illustrating an example of an internal configuration of a container holding unit according to the second embodiment of the present invention. In FIG. 7(a), a first holding wall portion and a second holding wall portion of the container holding unit 42 are omitted. In FIG. 7(b), a pair of light transmission wall portions of the container holding unit 42 is omitted. Positions of a pair of openings 46 are illustrated by a broken line.

The ultrasonic irradiation unit 43 is provided on the inner wall surface of the first holding wall portion of the container holding unit 42. One or more pushing units 45 are provided on the inner wall surface of the second holding wall portion of the container holding unit 42. The pushing unit 45 is formed of, for example, an elastic material such as a spring or rubber. The container 41 inserted into the container holding unit 42 is pushed in a direction of the first holding wall portion by a pushing unit 45 and is closely adhered to the oscillation surface of the ultrasonic irradiation unit 43.

A distance L2 between the inner wall surfaces of the pair of light transmission wall portions constituting the container holding unit 42 is set to be shorter than the wavelength of the ultrasonic wave output from the ultrasonic irradiation unit 43. The distance L between the inner wall surfaces of the light transmission wall portions of the container 41 is set to be shorter than the distance L2. Accordingly, similar to the first embodiment, a sufficiently wide transparent region which allows light to pass straightly through from the light source 10 to the light receiving unit 30 is formed inside the container 41. The pair of the openings 46 is disposed in such a way that light irradiated from the light source 10 is passed through a measurement region T within the transparent region formed within the container 41 in the Y direction and is received by the light receiving unit 30.

In the optical analysis system 200 of the second embodiment, the ultrasonic irradiation unit 43 is provided on the container holding unit 42 and the container 41 is detachable to the container holding unit 42. With this, the plurality of containers 41 can be easily exchanged and thus, for example, analysis of a plurality of kinds of samples can be efficiently conducted.

[Third Embodiment]

An optical analysis system according to a third embodiment includes an agitation tank. In the following, description will be mainly made on differences between the third embodiment and the first embodiment.

Figure 8:
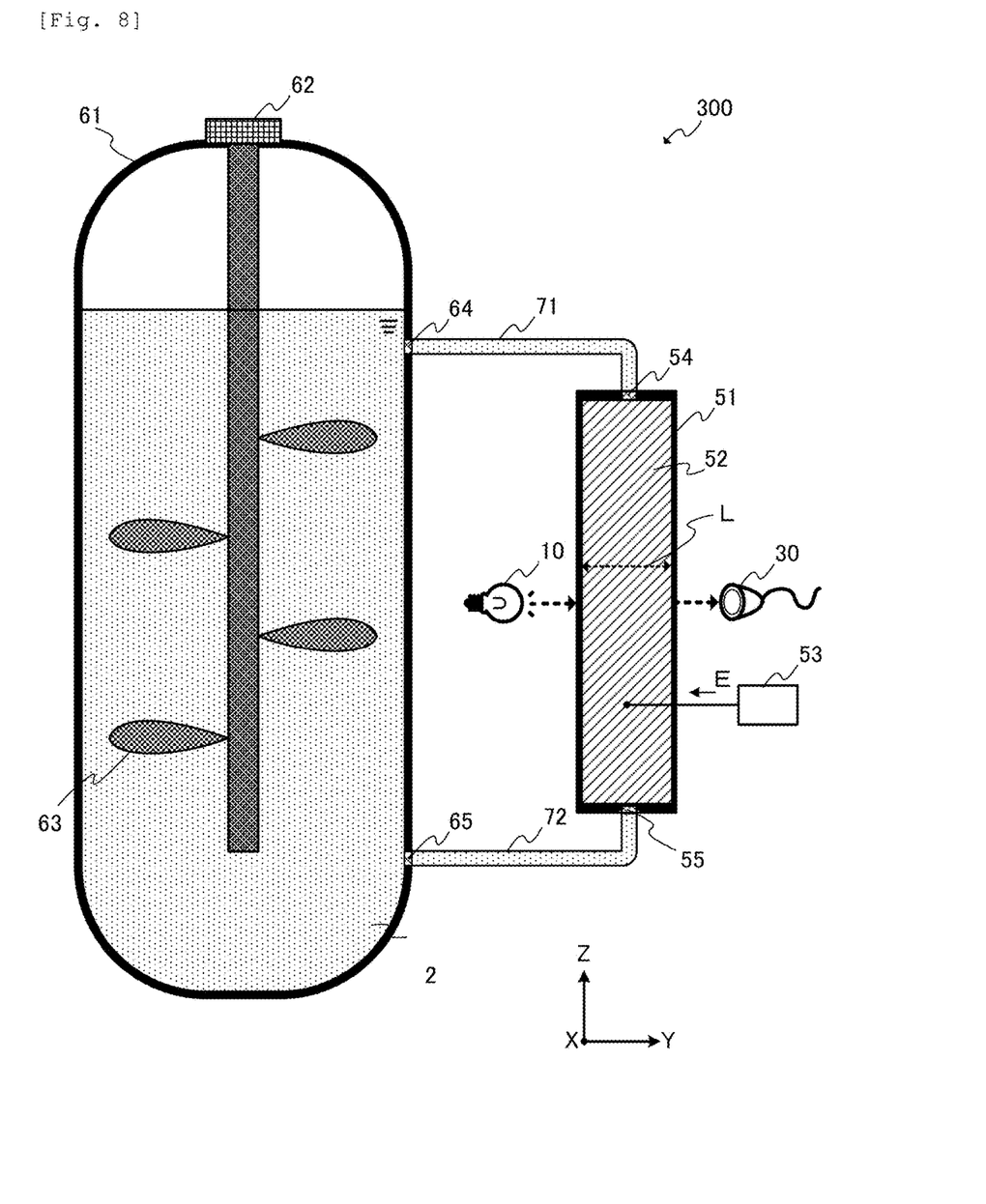
FIG. 8 is a diagram illustrating an example of a configuration of an optical analysis system according to a third embodiment of the present invention.

FIG. 8 is a diagram illustrating an example of a configuration of an optical analysis system according to the third embodiment. An optical analysis system 300 includes the light source 10, a container 51, an ultrasonic irradiation unit 52, a control unit 53, and the light receiving unit 30. The optical analysis system 300 further includes an agitation tank 61, a bypass 71, and a bypass 72. The configurations of the light source 10, the ultrasonic irradiation unit 52, the control unit 53, and the light receiving unit 30 are the same as those of the first embodiment.

A process of manufacturing chemicals or the like includes a process of agitating a suspension by an agitator or mixing the suspension with other materials. In the optical analysis system 300 of the present embodiment, the agitation tank 61 of the agitator and the container 51 are connected to the bypass 71 and the bypass 72 to circulate a sample 2 having a material suspended.

The agitation tank 61 includes a motor 62 rotating a rotating shaft and one or more agitating blades 63 provided at the periphery of the rotating shaft. The agitation tank 61 is provided with an outflow port 64 connected to one end of the bypass 71 and an inflow port 65 connected to one end of the bypass 72.

The container 51 is basically configured to be similar to that of the first embodiment. However, the container 51 is connected to the bypass 71 and the bypass 72. Specifically, the container 51 is provided with an inflow port 54 connected to the other end of the bypass 71 and an outflow port 55 connected to the other end of the bypass 72. In an example of FIG. 8, the inflow port 54 is provided on an upper wall portion (parallel to the XY plane) of the container 51 and the outflow port 55 is provided on an lower wall portion (parallel to the XY plane) of the container 51.

The sample 2 which is the suspension within the agitation tank 61 flows out of the outflow port 64 and flows into the container 51 through the bypass 71 and the inflow port 54. The sample 2 flowed into the container 51 flows out of the outflow port 55 and flows into the agitation tank 61 through the bypass 72 and the inflow port 65. As such, the sample 2 is circulated within the optical analysis system 300.

Figure 9:
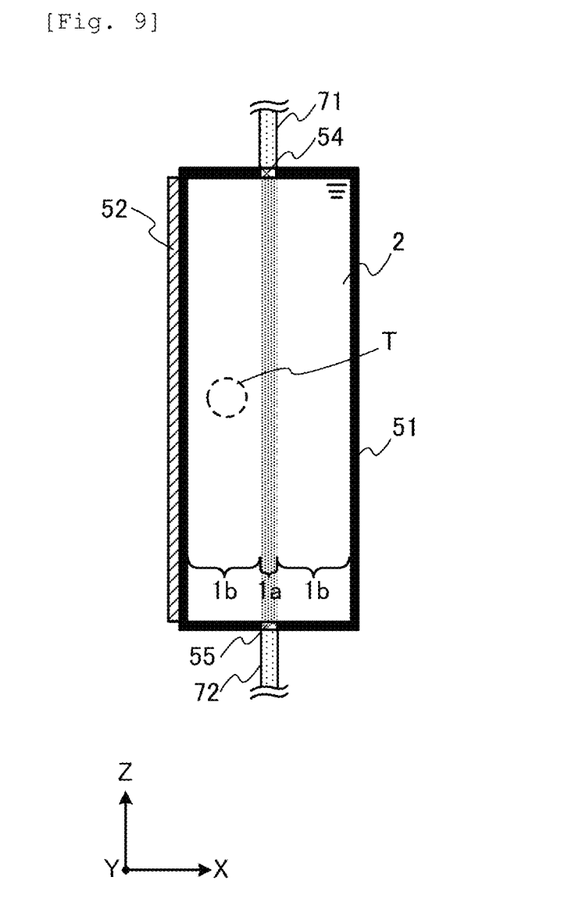
FIG. 9 is a diagram illustrating an operation principle of the optical analysis system according to the third embodiment of the present invention.

FIG. 9 is a diagram illustrating an operation principle of the optical analysis system according to the third embodiment of the present invention.

In a state where the sample 2 flows from the inflow port toward the outflow port 55 within the container 51, the ultrasonic irradiation unit 52 irradiates the ultrasonic wave. Then, similar to the first embodiment, the flocculation region 1a and the transparent region 1b periodically appear. Agitation by the agitator may be controlled so that the flow of the sample 2 is stopped in ultrasonic wave irradiation.

In the optical analysis system 300 according to the third embodiment, the sample 2 is circulated in a circulation system in which the agitation tank 61 and the container 51 are connected with each other and thus, for example, it is possible to perform component analysis while manufacturing the sample 2. It is possible to eliminate a work for exchanging the sample 1 as in the first embodiment. It is possible to eliminate a work for exchanging the container 41 as in the second embodiment.

[Fourth Embodiment]

The optical analysis system according to a fourth embodiment is different from the third embodiment in that the sample 2 is not circulated. In the following, description will be mainly made on differences between the fourth embodiment and the third embodiment.

Figure 10:
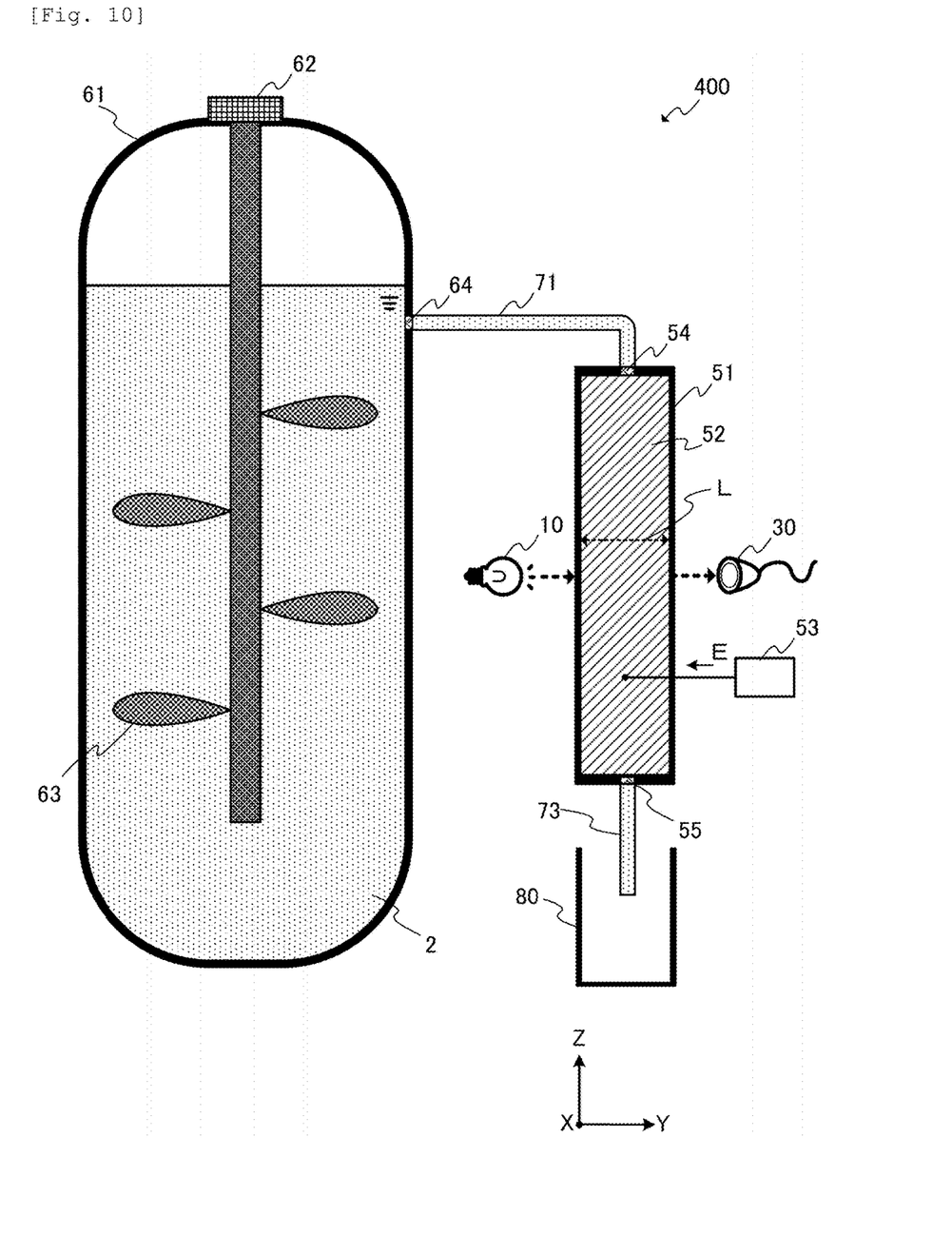
FIG. 10 is a diagram illustrating an example of a configuration of an optical analysis system according to a fourth embodiment of the present invention.

FIG. 10 is a diagram illustrating an example of a configuration of an optical analysis system according to a fourth embodiment. The optical analysis system 400 includes a bypass 73 instead of the bypass 72. The agitation tank 61 is not provided with the inflow port 65.

The outflow port 55 of the container 51 is connected to one end of the bypass 73. The other end of the bypass 73 is connected to a recovery system 80 installed outside the optical analysis system 400 or is opened. The recovery system 80 may be, for example, a discharge container and further, may be an analysis system for performing another analysis.

The sample 2 within the agitation tank 61 flows out of the outflow port 64 and flows into the container 51 through the bypass 71 and the inflow port 54. The sample 2 flowed into the container 51 flows out of the outflow port 55 and is discharged to the recovery system 80 through the bypass 73.

In the optical analysis system 400 according to the fourth embodiment, the sample 2 irradiated with the ultrasonic wave or light in the container 51 is discharged outside the system. With this, in a case where the sample 2 is deteriorated or is likely to be deteriorated by irradiation of the ultrasonic wave and light, it is possible to prevent the sample 2 within the agitation tank 61 from being deteriorated.

The present invention is not limited to the embodiments described above, but includes various modification examples. For example, the embodiments described above are described in detail in order to make the present invention easier to understand and is not necessarily limited to an embodiment in which all configuration described are included. Also, it is possible to replace a portion of a configuration of a certain embodiment with a configuration of another embodiment and it is possible to add a configuration of another embodiment to a configuration of a certain embodiment. Also, it is possible to add, delete, and replace of a configuration of another configuration, with respect to a portion of a configuration of a certain embodiment.

The present invention can be applied to optical analysis of an emulsion or the like, in addition to optical analysis of a suspension. Liquid fine particles dispersed in the emulsion liquid are flocculated in the node or the antinode of the ultrasonic wave. For example, oil particles are flocculated in the antinode in the emulsion in which oil particles are dispersed in water.

The present invention can be provided not only by the optical analysis system but also by various contents such as an optical analysis apparatus or an optical analysis method. For example, the light source, the container, the ultrasonic irradiation unit, the control unit, and the light receiving unit can be realized in the optical analysis apparatus.

REFERENCE SIGNS LIST 1, 2: sample
1a: flocculation region
1b: transparent region
10: light source
21, 41, 51: container
22, 43, 52: ultrasonic irradiation unit
23, 44, 53: control unit
30: light receiving unit
42: container holding unit
45: pushing unit
46: opening
54, 65: inflow port
55, 64: outflow port
61: agitation tank
62: motor
63: agitating blade
71, 72, 73: bypass
80: recovery system
100, 200, 300, 400: optical analysis system
E: electrical signal
L: distance (optical path length)
p1: node
p2: antinode
T: measurement region
w: standing wave

The invention claimed is:

1. An optical analysis system that irradiates a liquid sample with light and analyzes a component of the sample using transmitted light transmitted through the sample, the optical analysis system comprising:
   a container that accommodates the sample; and
   an ultrasonic oscillator that irradiates an ultrasonic wave for exciting the sample; and
   a container holder that detachably holds the container,
   wherein the container includes a pair of light transmission wall portions between which the sample is disposed and which has light transmissivity,
   one of the light transmission wall portions and the other of the light transmission wall portions are disposed to be separated from each other at a distance shorter than a wavelength of the ultrasonic wave,
   the ultrasonic oscillator is disposed so as to cause the ultrasonic wave to be irradiated in a direction different from that of the light,
   the container holder includes a pair of wall portions between which the container in a state of being held is disposed,
   a pair of openings allowing the light to pass through is provided on the pair of wall portions,
   the container holder includes a first holding wall portion and a second holding wall portion between which the container in a state of being held is disposed, and
   the ultrasonic oscillator is disposed on an inner wall surface of the first holding wall portion between the container in a state of being held and the first holding wall portion.

2. The optical analysis system according to claim 1, wherein the container includes a pair of wall portions between which the sample is disposed.

3. The optical analysis system according to claim 1, wherein the container holder is formed of an opaque material.

4. The optical analysis system according to claim 1, further comprising:
   a first bypass that causes the sample to flow into the container; and
   a second bypass that causes the sample to flow out of the container,
   wherein the container includes an inflow port connected to one end of the first bypass and an outflow port connected to one end of the second bypass.

5. The optical analysis system according to claim 4, further comprising:
   an agitation tank that agitates the sample,
   wherein the other end of the first bypass is connected to an outflow port provided on the agitation tank, and
   the other end of the second bypass is connected to an inflow port provided on the agitation tank.

6. The optical analysis system according to claim 4, further comprising:
   an agitation tank that agitates the sample,
   wherein the other end of the first bypass is connected to the outflow port provided on the agitation tank, and
   the other end of the second bypass is connected to an external recovery system.

7. The optical analysis system according to claim 1, wherein the sample is a suspension or an emulsion.

8. An optical analysis method in which a liquid sample is irradiated with light and a component of the sample is analyzed using transmitted light transmitted through the sample, the optical analysis method comprising:
   preparing a container, detachably held by a container holder, which accommodates the sample and includes a pair of light transmission wall portions between which the sample in a state of being accommodated is disposed and which has light transmissivity;
   accommodating the sample in the container; and
   irradiating the sample with an ultrasonic wave, output from an ultrasonic oscillator, having a wavelength longer than a distance between one of the light transmission wall portions and the other end of the light transmission wall portions and exciting the sample; wherein
   the ultrasonic oscillator is disposed so as to cause the ultrasonic wave to be irradiated in a direction different from that of the light,
   the container holder includes a pair of wall portions between which the container in a state of being held is disposed, a pair of openings allowing the light to pass through being provided on the pair of wall portions, the container holder includes a first holding wall portion and a second holding wall portion between which the container in a state of being held is disposed, and the ultrasonic oscillator is disposed on an inner wall surface of the first holding wall portion between the container in a state of being held and the first holding wall portion.

* * * * *